United States Patent [19]

Gaffney

[11] Patent Number: 4,560,823
[45] Date of Patent: Dec. 24, 1985

[54] HYDROCARBON DEHYDROGENATION
[75] Inventor: Anne M. Gaffney, West Chester, Pa.
[73] Assignee: Atlantic Richfield Company, Los Angeles, Calif.
[21] Appl. No.: 600,651
[22] Filed: Apr. 16, 1984
[51] Int. Cl.[4] .............................................. C07C 5/327
[52] U.S. Cl. .................................... 585/654; 585/656; 585/444; 585/658
[58] Field of Search ............... 585/654, 656, 658, 661, 585/444

[56] References Cited
U.S. PATENT DOCUMENTS

| | | | |
|---|---|---|---|
| 3,118,007 | 1/1964 | Krönig et al. | 585/617 |
| 3,210,436 | 10/1965 | Bajars et al. | 585/658 |
| 3,670,042 | 6/1972 | Croce et al. | 585/658 |
| 3,793,392 | 2/1974 | Martin | 585/661 |
| 4,454,363 | 6/1984 | Teng et al. | 585/428 |

Primary Examiner—Mark L. Bell
Assistant Examiner—Cynthia A. Prezlock
Attorney, Agent, or Firm—Craig E. Larson

[57] ABSTRACT

A method for dehydrogenating dehydrogenatable hydrocarbons which comprises contacting said hydrocarbon with an oxide of Ce having combined therewith an amount of alkali and/or alkaline earth metal which is sufficient to improve the selectivity to dehydrogenated hydrocarbon products. The oxide is reduced by the contact which is carried at about 500° to 1000° C. Reducible oxides of Ce are regenerated by oxidizing the reduced composition with molecular oxygen. The oxide $CeO_2$ is particularly effective in the process.

13 Claims, No Drawings

HYDROCARBON DEHYDROGENATION

BACKGROUND OF THE INVENTION

This invention relates to dehydrogenation of dehydrogenatable hydrocarbons. This invention more particularly relates to oxidative dehydrogenation processes.

SUMMARY OF THE INVENTION

It has now been found that dehydrogenatable hydocarbons may be dehydrogenated to dehydrogenated hydrocarbon products by contacting a hydrocarbon-containing gas with a solid comprising: (1) a reducible oxide of cerium and (2) at least one member of the group consisting of alkali metals, alkaline earth metals, and compounds thereof. Alkali metals are selected from the group consisting of Li, Na, K, Rb and Cs. Alkaline earth metals are selected from the group consisting of Mg, Ca, Sr and Ba.

Dehydrogenatable hydrocarbons are desirably contacted with the solid at a temperature within the range of about 500° to 1000° C. The atomic ratio of cerium to alkali or alkaline earth metal is desirably within the range of about 1–15:1. The cerium oxide is reduced by contact with the hydrocarbon and is reoxidizable by contact with an oxygen-containing gas.

Contacting dehydrogenatable hydrocarbons with oxides of Ce in the absence of an alkali or alkaline earth metal produces predominantly combustion products ($CO_x$). However, it has been found that incorporating an alkali metal or alkaline earth metal into the contact solid substantially reduces the formation of combustion products and improves dehydrogenated hydrocarbon product selectivity.

DETAILED DESCRIPTION OF THE INVENTION

Reducible oxides of Ce can be supplied from a variety of known sources. The term "reducible" is used to identify those oxides which are reduced by contact with hydrocarbon at temperatures within the range of about 500° to 1000° C. A preferred oxide is $CeO_2$.

The contact solid employed in the present process contains, in addition to a reducible oxide of Ce, at least one alkali metal or alkaline earth metal. Alkali metals are preferred. Sodium and lithium are presently preferred alkali metals. The amount of alkali/alkaline earth metal incorporated into the contact solid is not narrowly critical. The preferred atomic ratio of the reducible cerium oxide component (expressed as the metal, Ce) to the alkali/alkaline earth metal component (expressed as the metal, e.g., Na) is within the range of about 1–15:1, more preferably within the range of about 1–3:1.

The contact solid may also contain other components commonly referred to as oxidative dehydrogenation agents (or catalysts). Oxidative dehydrogenation agents generally comprise at least one oxide of at least one metal, which oxides when contacted with dehydrogenatable hydrocarbons at dehydrogenation conditions (e.g., at a temperature selected within the range of about 500° to 1000° C.) produce dehydrogenated hydrocarbon products, co-product water, and a reduced metal oxide. The composition thus contains at least one reducible oxide of at least one metal. The term "reducible" is used to identify those oxides of metals which are reduced by contact with the hydrocarbons at dehydrogenation conditions (e.g., at temperatures selected within the range of about 500°–1000° C.). The term "oxide(s) of metal(s)" includes: (1) one or more metal oxides (i.e., compounds described by the general formula $M_xO_y$ wherein M is a metal and the subscripts $x$ and $y$ designate the relative atomic proportions of metal and oxygen in the composition) and/or (2) one or more oxygen-containing metal compounds, provided that such oxides and compounds have the capability of performing to produce dehydrogenated hydrocarbon products as set forth herein.

One class of preferred oxidative dehydrogenation agents comprises reducible oxides of metals selected from the group consisting of Mn, Sn, In, Ge, Sb, Pb, and Bi and mixtures thereof. Particularly effective oxidative dehydrogenation agents have been found to comprise a reducible oxide of manganese and mixtures of a reducible oxide of manganese with other oxidative dehydrogenation agents.

It is within the scope of the present invention to include other effective oxidative dehydrogenation agent components with the combined cerium oxide/alkali-alkaline earth metal system of the present invention. Thus, the cerium oxide/ alkali-alkaline earth metal system may also contain a reducible oxide selected from the group consisting of Mn, Sn, In, Ge, Sb, Pb, Bi and mixtures thereof.

Preferably, the contact solid employed in the process of the present invention comprises: (1) a reducible oxide of Ce; (2) at least one member of the group consisting of alkali metals, alkaline earth metals, and compounds thereof; and (3) at least one reducible oxide of at least one metal selected from the group consisting of Mn, Sn, In, Ge, Sb, Pb, Bi and mixtures thereof. In a preferred embodiment of this specific class of solids, the third component is a reducible oxide of Mn. In a further preferred embodiment of this specific class of solids, the second component is sodium and compounds thereof. In a particularly preferred embodiment of this specific class of solids, the first component is provided as a support for the second and third components.

It is also within the scope of the present invention to include at least one phosphorus component in the solid. However, the contact solid of this invention is effective in the absence of phosphorus.

While the exact composition of the contact solids is more complex, the solids employed in the process of this invention may be described by the following empirical expression:

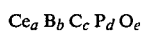

$$Ce_a\ B_b\ C_c\ P_d\ O_e$$

wherein B is selected from the group consisting of alkali and alkaline earth metals; C is selected from the group consisting of Mn, Sn, In, Ge, Pb, Sb, Bi and mixtures thereof; a, b, c, d and e indicate the atomic ratio of each component; and when a is 10, b is within the range of about 0.5–10, c is within the range of about 0–10, d is within the range of about 0–10, and e has a value which is determined by the valences and proportions of the other elements present.

These components may be associated with other support materials. However, in a presently preferred embodiment, a reducible oxide of Ce is employed as a support for the other components of the solids. While use of other supports is within the scope of this invention, it has been found that materials such as silica and alumina tend to deactivate the cerium component via the formation of silicates and aluminates.

The contact solids employed in this invention can be prepared by any suitable method. Conventional methods such as precipitation, co-precipitation, impregnation, or dry-mixing can be used. Supported solids may be prepared by methods such as adsorption, impregnation, precipitation, co-precipitation, and dry-mixing. When phosphorus is incorporated in the agent, it is desirable to provide it in the form of a phosphate of an alkali metal or an alkaline earth metal. Substantially any compound of these elements can be employed in the preparation of the promoted dehydrogenation agent.

A suitable method of preparation is to impregnate a support with solutions of compounds of the desired metals. Suitable compounds useful for impregnation include the acetates, acetylacetonates, oxides, carbides, carbonates, hydroxides, formates, oxalates, nitrates, phosphates, sulfates, sulfides, tartrates, fluorides chlorides, bromides, or iodides. After impregnation the preparation is dried to remove solvent and the dried solid is prepared for use by calcining, preferably in air, at a temperature selected within the range of about 300° to 1200° C. Particular calcination temperatures will vary depending upon the particular metal compound or compounds employed.

If phosphorus is used, the alkali/alkaline earth metal and phosphorus are preferably added to the composition as compounds containing both P and alkali/alkaline earth metals. Examples are the orthophosphates, metaphosphates, and pyrophosphates of alkali/alkaline earth metals. Pyrophosphates have been found to give desirable results. Sodium pyrophosphate is particularly preferred.

Regardless of how the components of the contact solid are combined, the resulting composite generally will be dried and calcined at elevated temperatures.

The dehydrogenatable hydrocarbon feedstock employed in the method of this invention is intended to include a wide variety of hydrocarbons: e.g., $C_{2}+$ alkanes, cycloalkanes, olefins, alkylaromatics, etc. The dehydrogenated product will of course depend in part on the feedstock selected. For example, alkanes may be dehydrogenated to form olefins, diolefins, alkynes, etc., and olefins may be dehydrogenated to form diolefins, alkynes, etc. Thus, potential uses for the present process include the following conversions:

(1) ethane→ethylene→acetylene;
(2) propane→propylene;
(3) butane→butene→butadiene;
(4) 2-methylbutane→2-methylbutenes→isoprene; and
(5) toluene→stilbene.

One preferred class of feedstocks comprises C2- C5 alkanes.

Operating temperatures for the contacting of hydrocarbon-containing gas and the rare earth/alkali-alkaline earth metal solid are generally within the range of about 500° to 1000° C. If reducible oxides of metals such as In, Ge, or Bi are present in the solid, the particular temperature selected may depend, in part, on the particular reducible metal oxide(s) employed. Thus, reducible oxides of certain metals may require operating temperatures below the upper part of the recited range to minimize sublimation or volatilization of the metals (or compounds thereof) during methane contact. Examples are: (1) reducible oxides of indium, (operating temperatures will preferably not exceed about 850° C.); (2) reducible oxides of germanium (operating temperatures will preferably not exceed about 850° C.); and (3) reducible oxides of bismuth (operating temperatures will preferably not exceed about 850° C.).

Operating pressures for the hydrocarbon contacting step are not critical to the presently claimed invention.

Contacting dehydrogenatable hydrocarbons and the solid comprising a cerium oxide/alkali-alkaline earth metal composite to form dehydrogenated hydrocarbons also produces a reduced metal oxide and co-product water. The exact nature of the reduced metal oxides are unknown, and so are referred to herein as "reduced metal oxides". Regeneration of a reducible metal oxide is readily accomplished by contacting such reduced materials with oxygen (e.g., an oxygen-containing gas such as air) at elevated temperatures, preferably at a temperature selected within the range of about 300° to 1200° C., the particular temperature selected depending on the metal(s) included in the solid.

In carrying out the present process, a single reactor apparatus containing a fixed bed of solids may be used with intermittent or pulsed flow of a first gas comprising dehydrogenatable hydrocarbons and a second gas comprising oxygen (e.g., oxygen, oxygen diluted with an inert gas, or air, preferably air). The hydrocarbon contacting step and the oxygen contacting step may also be performed in physically separate zones with solids recirculating between the two zones.

Thus, a suitable method for dehydrogenating dehydrogenatable hydrocarbons comprises: (a) contacting a gas comprising said hydrocarbon and particles comprising a reducible Ce oxide/alkali-alkaline earth metal composite to form dehydrogenated hydrocarbon products, co-product water, and reduced metal oxide; (b) removing particles comprising reduced metal oxide from the first zone and contacting the reduced particles in a second zone with an oxygen-containing gas to form particles comprising a reducible Ce oxide/alkali-alkaline earth metal composite; and (c) returning the particles produced in the second zone to the first zone. The steps are preferably repeated at least periodically, and more preferably the steps are continuous. In the more preferred embodiment solids are continuously circulated between at least one methane-contact zone and at least one oxygen-contact zone.

Particles comprising a reducible Ce oxide/alkali-alkaline earth metal composite which are contacted with hydrocarbon may be maintained as fluidized, ebullating, or entrained beds of solids. Preferably the hydrocarbon is contacted with a fluidized bed of solids.

Similarly, particles comprising reduced metal oxide which are contacted with oxygen may be maintained as fluidized, ebullating or entrained beds of solids. Preferably oxygen is contacted with a fluidized bed of solids.

In one more preferred embodiment of the present invention, hydrocarbon feedstock and particles comprising a promoted oxidative dehydrogenation agent are continuously introduced into a hydrocarbon contact zone maintained at dehydrogenation conditions. Gaseous reaction products from the methane contact zone (separated from entrained solids) are further processed—e.g., they are passed through a fractionating system wherein the desired hydrocarbon products are separated from unconverted hydrocarbon and combustion products. Unconverted hydrocarbon may be recovered and recycled to the hydrocarbon contact zone.

Particles comprising reduced metal oxide are contacted with oxygen in an oxygen contact zone for a time sufficient to oxidize at least a portion of the reduced oxide to produce a reducible metal oxide and to remove, i.e., combust, at least a portion of any carbonaceous deposit which may form on the particles in the hydrocarbon contact zone. The conditions of the oxygen contact zone will preferably include a temperature selected within the range of about 300° to 1200° C., pressures of up to about 30 atmospheres, and average particle contact time within the range of about 1 to 120 minutes. Sufficient oxygen is preferably provided to oxidize all reduced metal oxide to produce a reducible oxide and to completely combust any carbonaceous deposit material deposited on the particles. At least a portion of the particles comprising promoted oxidative dehydrogenation agent which are produced in the oxygen contact zone are returned to the hydrocarbon contact zone.

The rate of solids withdrawal from the hydrocarbon contact zone is desirably balanced with the rate of solids passing from the oxygen contact zone to the hydrocarbon contact zone so as to maintain a substantially constant inventory of particles in the hydrocarbon contact zone, thereby enabling steady state operation of the dehydrogenation system.

What is claimed is:

1. A method for dehydrogenating dehydrogenatable hydrocarbons which comprises:
   (a) continuously introducing and contacting in a first zone at a temperature within the range of about 500°–1000° C. a gas comprising said hydrocarbon and a solid consisting essentially of: (1) a reducible oxide of Ce and (2) at least one member of the group consisting of alkali earth metals, alkaline earth metals, and compounds thereof, said contacting producing dehydrogenated hydrocarbons, co-product water and solids comprising a reduced Ce oxide;
   (b) recovering dehydrogenated hydrocarbons;
   (c) continuously removing solids comprising reduced Ce oxide from the first zone and contacting the reduced solids with an oxygen-containing gas in a second zone to produce solids comprising a reducible Ce oxide; and
   (d) returning solids formed in the second zone to the first zone.

2. The method of claim 1 wherein component (2) of said solid recited in step (a) is selected from the group consisting of alkali metals and compounds thereof.

3. The method of claim 2 wherein the alkali metal is selected from the group consisting of Li, Na, K, Rb, Cs, and compounds thereof.

4. The method of claim 2 wherein the alkali metal is selected from the group consisting of sodium, sodium compounds and mixtures thereof.

5. The method of claim 2 wherein the alkali metal is selected from the group consisting of potassium, potassium compounds and mixtures thereof.

6. The method of claim 2 wherein the alkali metal is selected from the group consisting of lithium, lithium compounds and mixtures thereof.

7. The method of claim 1 wherein the reducible oxide is $CeO_2$.

8. The method of claim 1 wherein the atomic ratio of Ce to alkali/alkaline earth metal in said solid is within the range of about 1–15:1.

9. The method of claim 1 wherein the atomic ratio of Ce to alkali/alkaline earth metal in said solid is within the range of about 1–3:1.

10. The method of claim 1 wherein the said solid of step (a) consists essentially of an alkali metal or compound thereof on a support consisting essentially of said reducible Ce oxide.

11. The method of claim 1 wherein the temperature of step (c) is within the range of about 300° to 1200° C.

12. The method of claim 1 wherein the atomic ratio of Ce to alkali/alkaline earth metal in said solid is within the range of about 1–15:1.

13. The method of claim 1 wherein the atomic ratio of Ce to alkali/alkaline earth metal in said solid is within the range of about 1–3:1.

* * * * *